(12) United States Patent
Kam et al.

(10) Patent No.: US 9,674,447 B2
(45) Date of Patent: Jun. 6, 2017

(54) APPARATUS AND METHOD FOR ADAPTIVE COMPUTER-AIDED DIAGNOSIS

(71) Applicant: Samsung Electronics Co., Ltd., Suwon-si (KR)

(72) Inventors: Hye Jin Kam, Seongnam-si (KR); Ye Hoon Kim, Seoul (KR); Seung Chul Chae, Seoul (KR); Byung Kon Kang, Gwangju-si (KR); Ha Young Kim, Yongin-si (KR); Ki Yong Lee, Suwon-si (KR); Joo Hyuk Jeon, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 74 days.

(21) Appl. No.: 14/825,681

(22) Filed: Aug. 13, 2015

(65) Prior Publication Data

US 2016/0048737 A1 Feb. 18, 2016

(30) Foreign Application Priority Data

Aug. 14, 2014 (KR) .................. 10-2014-0106269

(51) Int. Cl.
| | | |
|---|---|---|
| G06K 9/62 | (2006.01) | |
| H04N 5/232 | (2006.01) | |
| G06T 7/00 | (2017.01) | |
| A61B 8/00 | (2006.01) | |
| A61B 8/08 | (2006.01) | |
| G06K 9/00 | (2006.01) | |

(52) U.S. Cl.
CPC ....... *H04N 5/23293* (2013.01); *A61B 8/4245* (2013.01); *A61B 8/5223* (2013.01); *G06K 9/00973* (2013.01); *G06K 9/6227* (2013.01); *G06K 9/6253* (2013.01); *G06T 7/0012* (2013.01); *A61B 8/469* (2013.01); *G06T 2207/10132* (2013.01); *G06T 2207/20008* (2013.01)

(58) Field of Classification Search
CPC .... G06K 9/6227; G06K 9/626; G06T 7/0012; G06T 2207/20004; G06T 2207/20008; A61B 8/48; A61B 8/5215; A61B 8/5223; G06F 19/345
See application file for complete search history.

(56) References Cited

U.S. PATENT DOCUMENTS

| | | | |
|---|---|---|---|
| 5,726,917 A | 3/1998 | Staaden | 364/560 |
| 2004/0093166 A1* | 5/2004 | Kil | 702/19 |
| 2013/0030281 A1* | 1/2013 | Suri | 600/410 |
| 2016/0253466 A1* | 9/2016 | Agaian et al. | G06F 19/345 382/128 |

* cited by examiner

*Primary Examiner* — Andrew W Johns
(74) *Attorney, Agent, or Firm* — Jefferson IP Law, LLP (57) ABSTRACT

An apparatus and method for adaptive computer-aided diagnosis (CAD) are provided. The adaptive CAD apparatus includes an image analysis algorithm selector configured to select an image analysis algorithm based on a speed of a probe or a resolution of a current image frame obtained by the probe; and an image analyzer configured to detect and classify a region of interest (ROI) in the current image frame using the selected image analysis algorithm.

23 Claims, 9 Drawing Sheets

APPARATUS AND METHOD FOR ADAPTIVE COMPUTER-AIDED DIAGNOSIS

CROSS-REFERENCE TO RELATED APPLICATION(S)

This application claims the benefit under 35 U.S.C. §119(a) of Korean Patent Application No. 10-2014-0106269, filed on Aug. 14, 2014, in the Korean Intellectual Property Office, the entire disclosure of which is incorporated herein by reference for all purposes.

BACKGROUND

1. Field

The following description relates to a medical image analysis technology, and particularly, to an adaptive computer-aided apparatus and method.

2. Description of Related Art

A computer-aided diagnosis (CAD) system refers to a system that analyzes medical images, such as ultrasound images, and displays a suspicious area in the medical images based on the analysis result, thereby assisting doctors in a diagnostic procedure. Diagnosis is a difficult process because of the uncertainty that is caused by human limitations in recognizing an illness. As such, utilizing a CAD system may prove to be advantageous because it not only reduces the probability of the aforementioned dilemma, but also lessens the doctor's workload with regard to deciphering individual diagnostic images.

However, a drawback of a CAD system is that it detects a region of interest (ROI) in each image frame and tracks or classifies the detected ROI in each image frame, thus making the CAD system difficult to operate in real time. In addition, since the CAD system generally employs the same detection/classification algorithm regardless of the speed of a moving probe or the resolution of an image, it is functionally impossible to promptly provide a detection/classification result or to perform real-time close examination on a salient area while the probe is moving.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided an adaptive computer-aided diagnostic (CAD) apparatus including: an image analysis algorithm selector configured to select an image analysis algorithm based on a speed of a probe or a resolution of a current image frame obtained by the probe; and an image analyzer configured to detect and classify a region of interest (ROI) in the current image frame using the selected image analysis algorithm.

The image analysis algorithm selector may be configured to select a first image analysis algorithm in response to the speed of the probe being equal to or greater than a predetermined threshold value, and to select a second image analysis algorithm in response to the speed of the probe being less than the predetermined threshold value.

The first image analysis algorithm may be a high-speed, low-accuracy algorithm relative to the second image analysis algorithm, and the second image analysis algorithm may be a low-speed, high-accuracy algorithm relative to the first image analysis algorithm.

The first image analysis algorithm and the second image analysis algorithm may be distinguished from each other based on at least one of the following factors: whether image-preprocessing is performed, a level of image-preprocessing performed, a size of a sub-image used in image analysis, a complexity of the image analysis algorithm, whether analysis results of pervious image frames are applied to the image analysis, a degree to which the analysis results of the previous image frames are utilized, and types and number of extractable features.

The image analysis algorithm selector may be configured to select the first image analysis algorithm in response to the resolution of the current image frame being lower than a predetermined threshold value, and to select the second image analysis algorithm in response to the resolution of the current image frame being equal to or higher than the predetermined threshold value.

The adaptive CAD apparatus may further include a speed detector configured to detect a speed of the probe.

The speed detector may be configured to detect the speed of the probe based on at least one of following factors: a difference between a sum of image intensities per pixel in the previous image frame and the sum of image intensities per pixel in the current image frame, a difference between a histogram of the current image frame and a histogram of the previous image frame, altering information between the previous and current image frames of a salient region, a sensor value obtained by an acceleration sensor equipped in or on the probe, and the resolution of the current image frame.

The adaptive CAD apparatus may further include a screen display configured to output an ROI detection result and an ROI classification result to a screen.

The screen display may be configured to further output to the screen information about the speed of the probe and the selected image analysis algorithm.

The information regarding the image analysis algorithm may include at least one of the following items: a type of image analysis algorithm, an indication of whether image-preprocessing is performed, a level of image-preprocessing performed, a size of a sub-image used in image analysis, a structure or complexity of the image analysis algorithm, an indication of whether analysis results of previous image frames are applied to the image analysis, a degree to which the analysis results of the previous image frames are utilized, and accuracy of the image analysis.

In another general aspect, there is provided an adaptive computer-aided diagnosis (CAD) method including: selecting, using an image analysis algorithm selector, an image analysis algorithm based on a speed of a probe or a resolution of a current image frame obtained by the probe; and detecting and classifying, using an image analyzer implementing the selected image analysis algorithm, a region of interest (ROI) in the current image frame.

The selecting of the image analysis algorithm may include selecting a first image analysis algorithm in response to the speed of the probe being equal to or greater than a predetermined threshold value, or selecting the second image analysis algorithm in response to the speed of the probe being less than the predetermined threshold value.

The first image analysis algorithm may be a high-speed, low-accuracy algorithm relative to the second image analysis algorithm, and the second image analysis algorithm may be a low-speed, high-accuracy algorithm relative to the first image analysis algorithm.

The first image analysis algorithm and the second image analysis algorithm may be distinguished from each other based on at least one of the following factors: whether image-preprocessing is performed, a level of image-preprocessing performed, a size of a sub-image used in image analysis, a complexity of the image analysis algorithm, whether analysis results of pervious image frames are applied to the image analysis, a degree to which the analysis results of the previous image frames are utilized, and types and a number of extractable features.

The selecting of the image analysis algorithm may include selecting the first image analysis algorithm in response to the resolution of the current image frame being lower than a predetermined threshold value, or selecting the second image analysis algorithm in response to the resolution of the current image frame being equal to or higher than the predetermined threshold value.

The adaptive CAD method may further include detecting a speed of the probe.

The detecting of the speed of the probe may be based on at least one of following factors: a difference between a sum of image intensities per pixel in a previous image frame and a sum of image intensities per pixel in the current image frame, a difference between a histogram of the current image frame and a histogram of the previous image frame, altering information between the previous and current image frames of a salient region, the sensor value obtained by an acceleration sensor equipped in or on the probe, and the resolution of the current image frame.

The adaptive CAD method may further include outputting an ROI detection result and an ROI classification result to a screen.

The adaptive CAD method may further include outputting to the screen information about the speed of the probe and the selected image analysis algorithm.

The information about the selected image analysis algorithm may include at least one of the following items: a type of image analysis algorithm, an indication of whether image-preprocessing is performed, a level of image-preprocessing performed, a size of a sub-image used in image analysis, a structure or complexity of the image analysis algorithm, an indication of whether analysis results of previous image frames are applied to the image analysis, a degree to which analysis results of the previous image frames are utilized, and an accuracy of the image analysis.

In yet another general aspect, an adaptive computer-aided diagnostic (CAD) apparatus comprises: a storage device configured to store image analysis algorithms; and a processor configured to select an image analysis algorithm among the image analysis algorithms based on a movement speed of a probe or a resolution of a current image frame obtained by the probe.

The image analysis algorithms may be classified based on a provided analysis accuracy and an analysis speed.

The image analysis algorithms may include a first image analysis algorithm that is classified as a high-speed, low-accuracy algorithm, and a second image analysis algorithm that is classified as a low-speed, high-accuracy algorithm.

Other features and aspects will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

An image analysis algorithm refers to an algorithm for analyzing an image to detect and classify a region of interest (ROI). The image analysis algorithm may include an image preprocessing algorithm, a lesion detection algorithm, and a lesion classification algorithm. Here, an ROI may include a lesion of unspecified nature, an area with unusual features, or a malignant lesion.

An image analysis algorithm may be classified, for example, as either) a high-speed, low-accuracy algorithm or a low-speed, high-accuracy algorithm. A high-speed, low-accuracy algorithm is faster in analyzing images, but produces a less accurate analysis result than a low-speed, high-accuracy algorithm, which has a slower analysis speed but produces a more accurate result.

In one example, an image analysis algorithm may be classified as either high-speed, low-accuracy or low-speed, high-accuracy based on whether the algorithm performs image-preprocessing, the level of image-preprocessing the algorithm performs, the size of a sub-image to be used in the image analysis, the complexity of the algorithm, whether analysis results of previous image frames are applied to the image analysis, and the types and number of extractable features in the image analysis.

Here, "features" that may be extracted in the image analysis refer to characteristics that help determine whether an ROI in an image is a lesion or not. For example, the features may include the shape, margin, echo pattern, orientation, boundary, and textual features of a lesion within an ROI.

Hereinafter, with reference to table 1, examples of both a high-speed, low-accuracy algorithm and a low-speed, high-accuracy algorithm are described.

TABLE 1

|  | High-speed, low-accuracy algorithm | Low-speed, high-accuracy algorithm |
|---|---|---|
| Image-preprocessing | None | Performs preprocessing (histogram equalization, median filtering, Gaussian filtering, maximum/minimum value filtering, etc.) |
|  | Performs partial preprocessing (e.g., histogram equalization) | Performs multi-stage preprocessing on images (histogram equalization, median filtering, Gaussian filtering, maximum/minimum value filtering, etc.) |
| Size of sub-image | One entire image | Entire image, set of patch images 1/16 in size |
|  | Entire image, set of patch images 1/16 in size | Entire image; sets of sliding windows at 1 pixel intervals, sliding windows in respective sets being 1/2, 1/4, and 1/16 in size |
| Complexity of Algorithm (including speed/accuracy) | Filtering-based high-speed, simple algorithm | Deep-learning based low-speed, high-accuracy algorithm |
|  | Deep-learning CNN structure (layer depth: 3) | Deep-learning based CNN structure (layer depth: 6) |
| Analysis result of previous image frame | Does not utilize information about analysis results of previous image frames | Utilizes information about analysis result of previous image frames (t-1, t-2, . . . , t-3) |
|  | Utilizes information about analysis results of previous image frame | Utilizes information about analysis results of previous image frames (t-1, t-2, . . . , t-3) and extracted features of a current image frame |

Referring to Table 1, the high-speed, low-accuracy algorithm and the low-speed, high-accuracy algorithm can be distinguished from each other based largely on four factors.

First, the differentiation between the high-speed, low-accuracy algorithm and the low-speed, high-accuracy algorithm may be based on whether image-preprocessing is performed and the level of preprocessing performed. For example, the high-speed, low-accuracy algorithm may not execute image-preprocessing, whereas the low-speed, high-accuracy algorithm may execute image-preprocessing (e.g., histogram equalization; the application of a median filter, Gaussian filter, maximum/minimum filter, and the like). In another example, the high-speed, low-accuracy algorithm may perform partial image-preprocessing (e.g., histogram equalization), while the low-speed, high-accuracy algorithm may perform multi-stage image preprocessing (e.g., after histogram equalization, filtering (utilizing a median filter, Gaussian filter, maximum/minimum filter, and the like).

In addition, the differentiation between the high-speed, low-accuracy algorithm and the low-speed, high-accuracy algorithm may be based on the size of the sub-image to be used in image analysis. For example, the high-speed, low-accuracy algorithm may only use an entire image in image analysis, whereas the low-speed, high-accuracy algorithm may use the entire image and a set of patch images, each being 1/16 in size, for example, compared to the original entire image. In another example, the high-speed, low-accuracy algorithm may use the entire image and a set of patch images, each being 1/16 in size, for example, compared to the original entire image, whereas the low-speed, high-accuracy algorithm may use the entire image along with sets of sliding windows, for example, at 1 pixel intervals, wherein the sliding windows in the sets are 1/2, 1/4, and 1/16 the size of the entire image.

Further, the differentiation between the high-speed, low-accuracy algorithm and the low-speed, high-accuracy algorithm may be based on the complexity/structure of the algorithm. For example, the high-speed, low-accuracy algorithm may be a filtering-based, high-speed, simple algorithm, whereas the low-speed, high-accuracy algorithm may be a deep-learning based, low-speed, high-accuracy algorithm. In another example, the high-speed, low-accuracy algorithm may be of a deep-learning, convolutional neural network (CNN) structure with a layer depth of 3, while the low-speed, high-accuracy algorithm may be of a deep-learning, CNN structure with a layer depth of 6.

Furthermore, the differentiation between the high-speed, low-accuracy algorithm and the low-speed, high-accuracy algorithm may be based on whether the analysis results of previous image frames are utilized in the image analysis, and the degree to which the analysis results are utilized. For example, the high-speed, low-accuracy algorithm may not utilize the analysis results of the previous image frames in the image analysis, while the low-speed, high-accuracy algorithm may utilize analysis results of n number of previous image frames (t-1, t-2, . . . , and t-n) in the image analysis. In another example, the high-speed, low-accuracy algorithm may only utilize the information about the analysis results of n number of previous image frames, while the low-speed, high-accuracy algorithm may utilize not only the analysis results of n number of previous image frames, but also features of a current image frame which were newly extracted based on the analysis results of n number of previous image frames.

Hereinafter, a computer-aided diagnosis apparatus will be described in detail with reference to FIG. 1.

Figure 1:
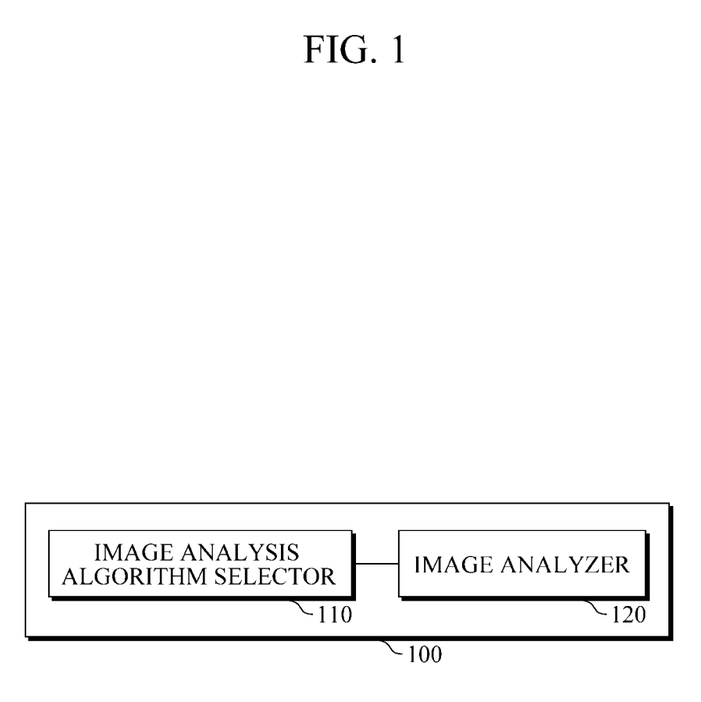
FIG. 1 is a block diagram illustrating an example of a computer-aided diagnosis (CAD) apparatus.

FIG. 1 is a block diagram illustrating an example of a computer-aided diagnosis (CAD) apparatus.

Referring to FIG. 1, the CAD apparatus 100 may include an image analysis algorithm selector 110 and an image analyzer 120.

The image analysis algorithm selector 110 may select an appropriate image analysis algorithm according to the movement speed of a moving probe or the resolution of a current image frame. The current image frame is a real-time image of a current frame that is being obtained by a probe.

For example, the image analysis algorithm selector 110 may select a high-speed, low-accuracy algorithm for use in analyzing the current image frame if the movement speed of the moving probe is equal to or greater than a predefined threshold, or the algorithm selector may select a low-speed, high-accuracy algorithm when the movement speed of the moving probe is lower than the predefined threshold.

In another example, the image analysis algorithm selector 110 may select the high-speed, low-accuracy algorithm for use in analyzing the current image frame if the resolution of the current image frame is lower than a predetermined threshold, or select the low-speed, high-accuracy algorithm if the resolution is equal to or higher than the predetermined threshold.

The image analyzer 120 analyzes the current image frame using the image analysis algorithm selected by the image analysis algorithm selector 110, and detects and classifies a region of interest.

Thus, according to the preceding description of FIG. 1, the CAD apparatus 100 may detect and classify a region of interest by either using a simple algorithm that can produce an optimal result within a unit time period when the probe is moving fast or the current image frame is of low resolution, or by using a complex algorithm that can enlarge a target image area through sophisticated image preprocessing and can very efficiently extract features with when the probe is moving slowly or the current image frame is of high resolution.

Figure 2:
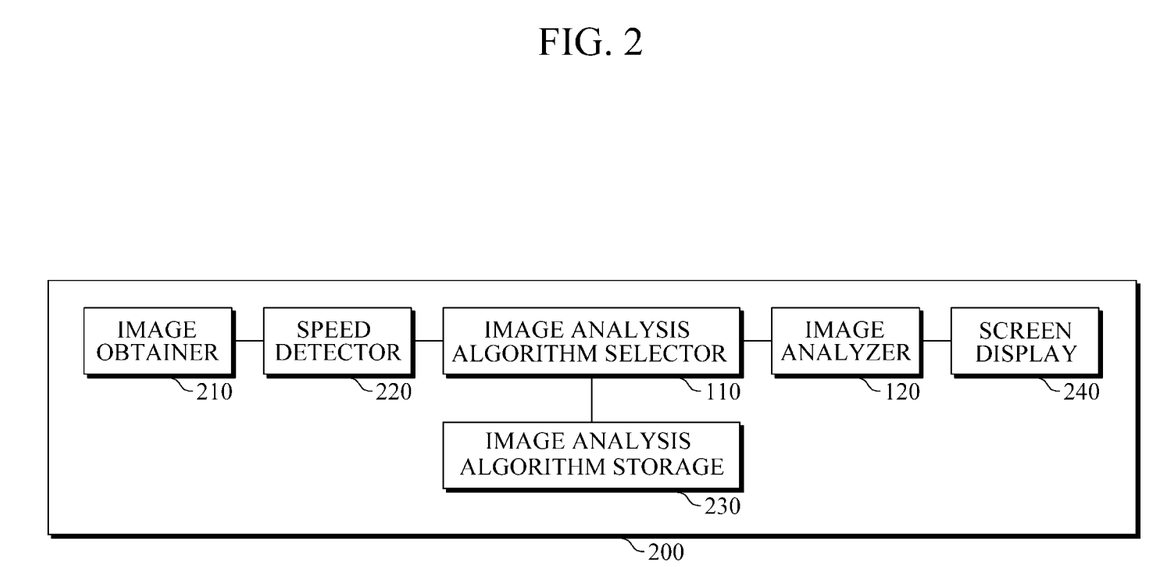
FIG. 2 is a diagram illustrating another example of a CAD apparatus.

FIG. 2 is a diagram illustrating another example of the CAD apparatus.

Referring to FIG. 2, a CAD apparatus 200 may further include an image obtainer 210, a speed detector 220, an image analysis algorithm storage 230, and a screen display 240, in addition to the elements of the CAD apparatus of FIG. 1.

The image obtainer 210 obtains ultrasound images of an affected part of a patient through a probe. The image obtainer 210 may obtain real-time ultrasound images on a frame-by-frame basis through the probe.

The speed detector 210 measures the movement speed of a probe.

For example, the speed detector 220 may measure the movement speed of a probe based on a difference between a sum of image intensities per pixel in a previous image frame and a sum of image intensities per pixel in a current image frame, whereby both frames are obtained by the probe. To elaborate, the speed detector 220 may perform image preprocessing to measure image intensities per pixel for the previous image frame and the current image frame, find a sum of the calculated image intensities per pixel for the previous image frame and a sum of the calculated image intensities per pixel for the current image frame, and then detect the speed of the probe based on the difference in the two sums.

In another example, the speed detector 220 may detect the movement speed of the probe based on a difference in histograms between the previous image frame and the current image frame. That is, the speed detector 220 may use a spectral analysis method to obtain the difference between the histogram of the current image frame and the histogram of the previous image frame, and then detect the movement speed of the probe based on the difference between the histogram of the current image frame and the histogram of the previous image frame when the value of this difference is greater than a given value.

In another example, the speed detector 220 may detect the movement speed of the probe based on altering information between the previous and current image frames of a salient region.

Also, the speed detector 220 may detect the movement speed of the probe based on a value obtained by a sensor equipped in or attached to the probe, for example, a 3-axis acceleration sensor.

In another example, the speed detector 220 may estimate the movement speed based on the resolution of the current image frame. If the resolution of the current image frame is lower than a predetermined threshold value, the speed detector 220 may infer that the movement speed of the probe is high; otherwise, if the resolution of the current image is equal to or higher than the predetermined threshold value, the speed detector 220 may infer that the speed of the probe is low. In the case in which the speed detector 220 infers, based on the resolution of the current image frame, that the movement speed of the probe is high, the image analysis algorithm selector 110 may select a high-speed, low-accuracy algorithm. In the case in which the speed detector 220 infers that the speed of the probe is low, the image analysis algorithm selector 110 may select a low-speed, high-accuracy algorithm.

The image analysis algorithm storage 230 may store image analysis algorithms.

The image analysis algorithm storage 230 may include various types of storage mediums, for example, flash memory, hard disks, multimedia card micro memory, card-type memory (e.g., SD or XD memory), RAM, SRAM (static RAM), ROM, electrically erasable programmable ROM (EEPROM), programmable ROM (PROM), magnetic tapes, magnetic disks, optical disks, and the like.

The screen display 240 may output the current image frame and the analysis result of the current image frame on a screen. The screen display 240 may output both the current image frame obtained in real-time by the probe to the screen as well as an image analysis result from the image analyzer 120. The image analysis result may be, for example, the detected ROI and a classification result for the detected ROI.

In addition, the screen display 240 may output information about the image analysis algorithm that has been selected according to information regarding the movement speed of the probe (e.g., whether the probe is moving at high speed (or high-speed mode) or low speed (or low-speed mode)) and/or the movement speed of the probe itself.

Here, the information about the image analysis algorithm may include the type of image analysis algorithm, whether image-preprocessing is performed, the level of image-preprocessing performed, the size of the sub-image used in the image analysis, the structure or complexity of the image analysis algorithm, whether analysis results of previous image frames are applied to the image analysis, the degree to which the analysis results of the previous image frames are utilized, and the accuracy of the image analysis.

Figure 3A:
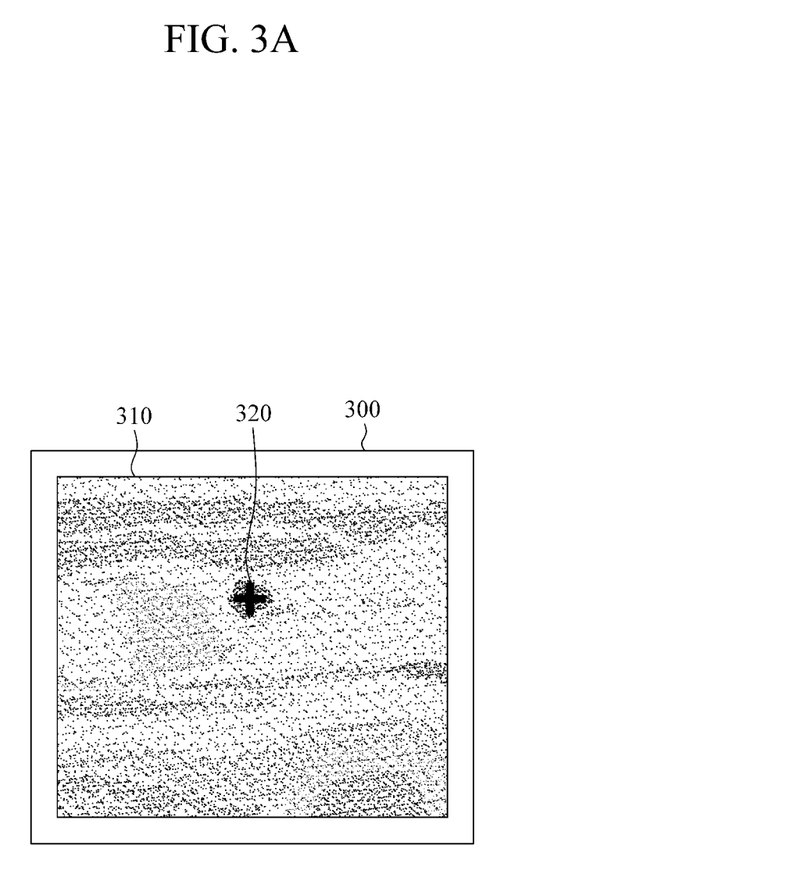
FIGS. 3A and 3B are diagrams illustrating examples of a screen onto which an output of a detected ROI is displayed.
Figure 3B:
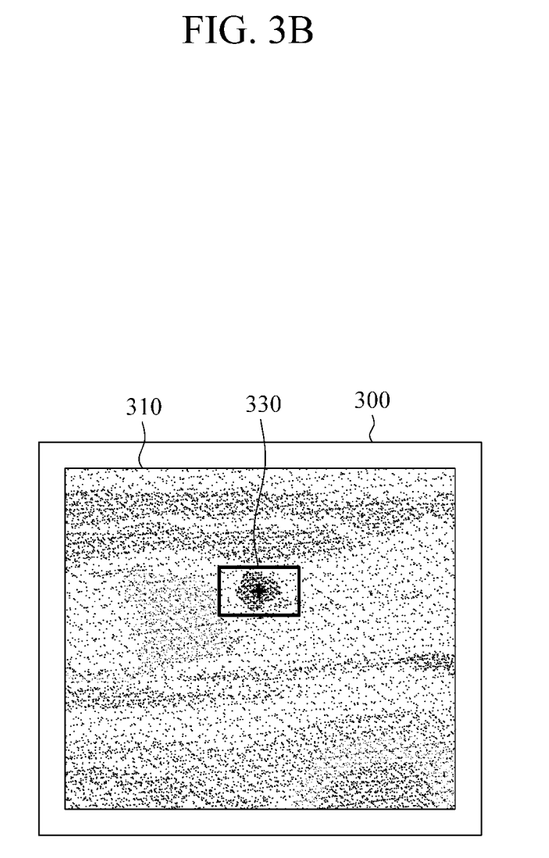

FIGS. 3A and 3B are diagrams illustrating examples of a screen onto which an output of a detected ROI is displayed.

The screen display 240 may output the detected ROI from the image analyzer 120 using various methods such that the ROI can be recognized by a user.

As shown in FIG. 3A, the screen display 240 may output a current image frame 310 on a screen 300, and mark the location of the detected ROI in the current image frame 310 with a cross 320.

As shown in FIG. 3B, the screen display 240 may output the current image frame 310 on the screen 300, and placing a box around the detected ROI in the current image frame 310 to indicate the ROI's location.

FIGS. 3A and 3B only illustrate examples of a method of outputting a detected ROI onto the screen display 240, and aspects of the present disclosure are not limited thereto. For example, the screen display 240 may indicate the ROI using a mark having a shape selected from various shapes, such as a circle, a triangle, or the like. Additionally, the ROI may be indicated using a color code in which a variety of colors may be used.

Figure 4:
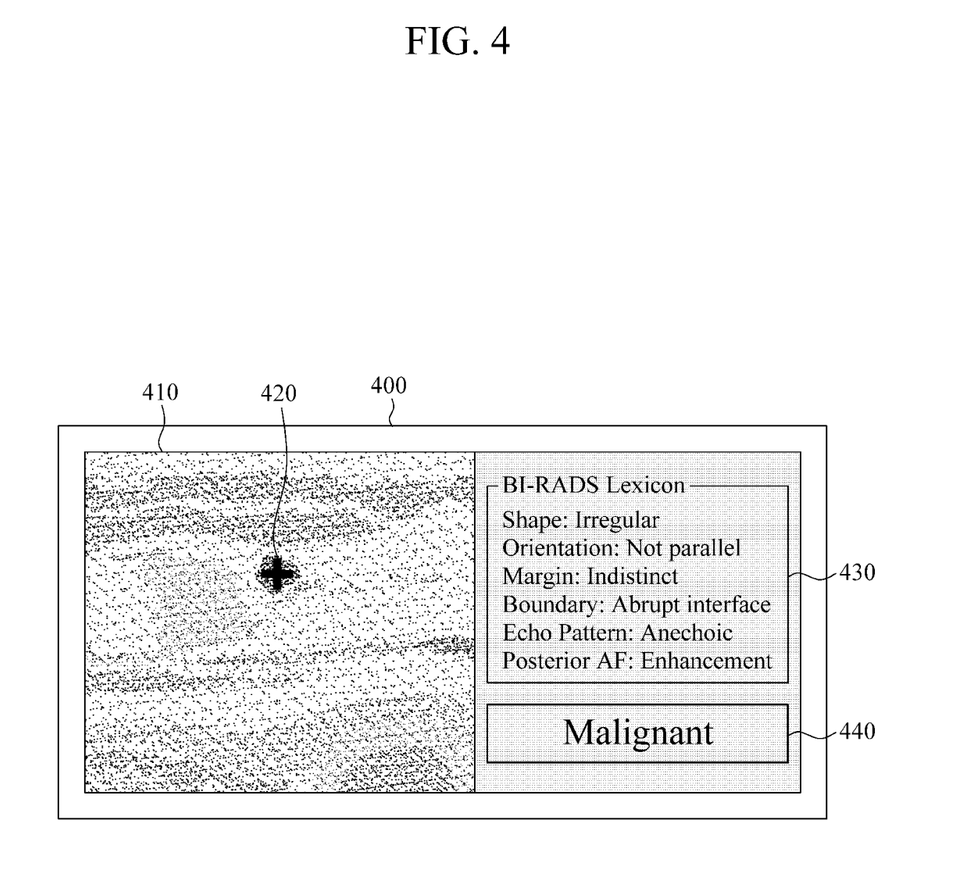
FIG. 4 is a diagram illustrating an example of a screen to which an ROI classification result is output.

FIG. 4 is a diagram illustrating an example of a screen 400 to which an ROI classification result is output. The example shown in FIG. 4 is the result of a breast ultrasound examination.

The screen display 240 may output the ROI classification result obtained by the image analyzer 120 using various methods so that the user can recognize the ROI.

Furthermore, the screen display 240 may output feature information 430 regarding the ROI in a designated area of the screen, the classification result 440 based on the feature information 430 that shows whether the ROI is malignant or benign, as well as the current image frame 410 shown with an identification mark 420 to indicate the location of an ROI.

Figure 5:
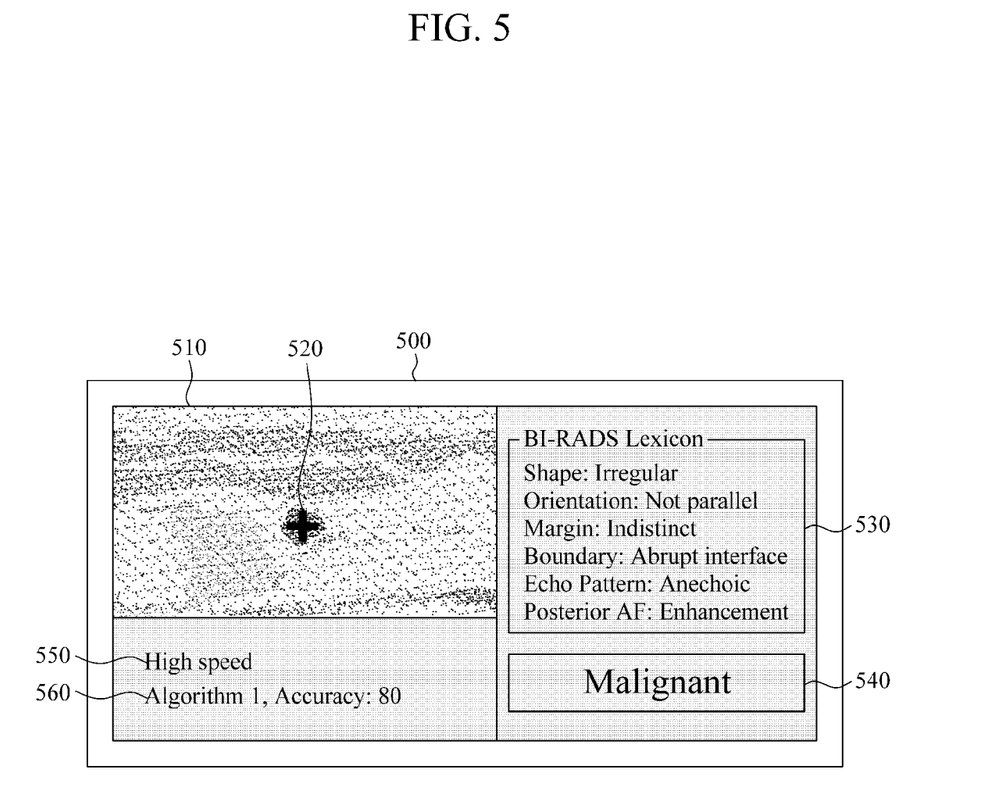
FIG. 5 is a diagram illustrating an example of a screen onto which information about the movement speed of a probe and information about an image analysis algorithm used in image analysis are output.

FIG. 5 is a diagram illustrating an example of a screen 500 onto which information about the speed of a probe and information about an image analysis algorithm used in image analysis are output.

The screen display 240 may output information about the movement speed of a probe along with image analysis algorithm information using various methods so that such information can be recognized by the user.

As shown in FIG. 5, the screen display unit 240 may output onto the screen 500 a current image frame 510 shown with an identification mark 520 to indicate the location of an ROI, as well as feature information 530 and the classification result 540 regarding the ROI. The screen display unit may also show, in a designated area of the screen, the movement speed information 550 of the probe and image analysis algorithm information 560.

Figure 6:
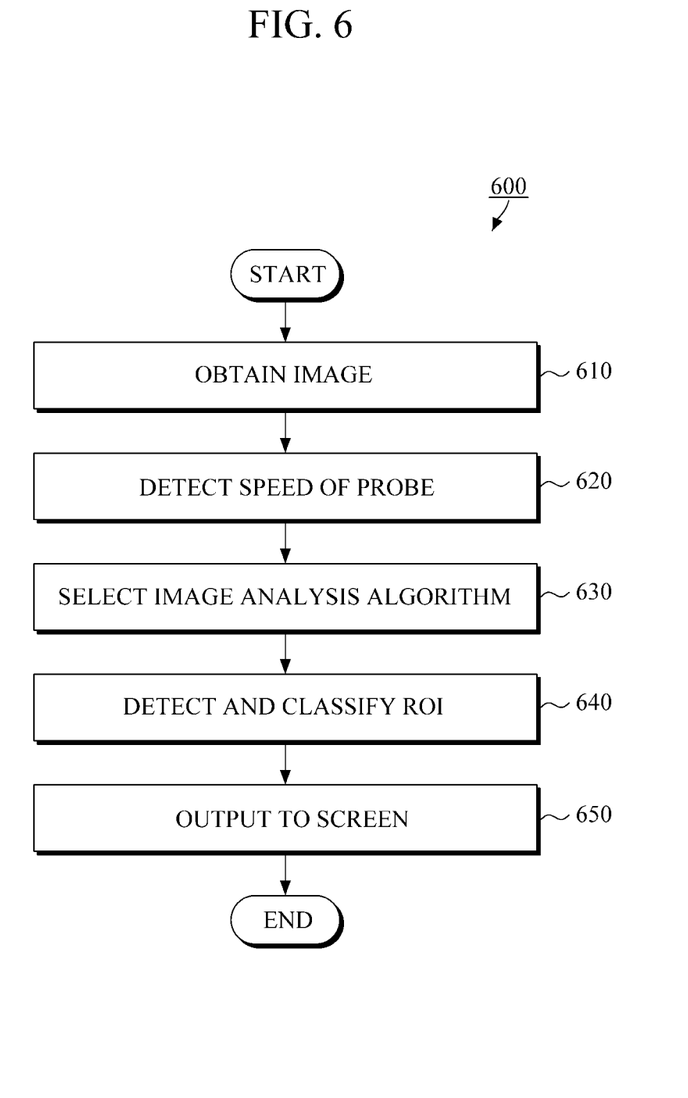
FIG. 6 is a flowchart illustrating an example of a computer-aided diagnosis (CAD) method.

FIG. 6 is a flowchart illustrating an example of a computer-aided diagnosis (CAD) method 600.

Referring to FIG. 6, in operation 610 of the method 600, ultrasound images of an affected part of a patient may be obtained by the probe.

In operation 620, a movement speed of the moving probe may be detected. For example, the CAD apparatus 200 may detect the movement speed of the moving probe based on: 1) the difference between the sum of image intensities per pixel in the current image frame and the sum of image intensities per pixel in a previous image frame; 2) the difference between the histogram of the current image frame and the histogram of the previous image frame; 3) the difference between information regarding a salient region in the previous image frame and information regarding the same region in the current image frame; 4) the sensor value obtained by an acceleration sensor equipped in the probe; and/or 5) the resolution of the current image frame.

In operation 630, an appropriate image analysis algorithm is selected in accordance with the speed of a probe or the resolution of a current image frame. At this time, the current image frame refers to an image of a current frame that is being obtained in real-time by the probe.

Then, in operation 640, the current image frame is analyzed using the selected image analysis algorithm to detect and then classify a ROI.

The CAD method 600 may further include an operation 650 in which the current image frame and the analysis result of the current image frame are both displayed onto the screen. At this time, information about the speed of the probe and/or information about the image analysis algorithm used in the image analysis may also be displayed.

Here, the image analysis algorithm information may include the type of image analysis algorithm used, whether image-preprocessing is performed, the level of image-preprocessing performed, the size of a sub-image used in the image analysis, the structure or complexity of the image analysis algorithm, whether analysis results of the previous image frames are applied to the image analysis, the degree to which the analysis results of the previous image frames are utilized, and the accuracy of the image analysis.

Figure 7:
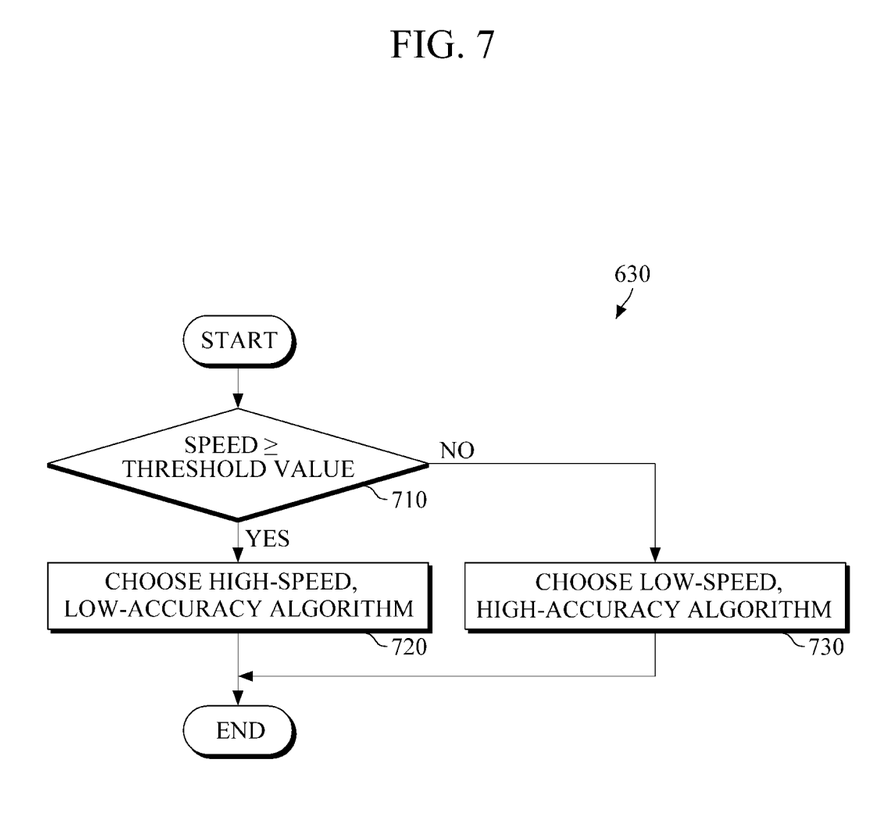
FIG. 7 is a flowchart illustrating an example of an operation of FIG. 6 in which an image analysis algorithm is selected.

FIG. 7 is a flowchart illustrating an example of operation 630 of FIG. 6 in which an image analysis algorithm is selected.

Referring to FIG. 7, the image analysis algorithm selection operation 630 may begin with operation 710 in which the movement speed of the probe is compared to a predetermined threshold value. If the movement speed of the probe is equal to or greater than the predetermined threshold value, a high-speed, low-accuracy algorithm is selected to be used in analysis of the current image frame in operation 720. If the movement speed of the probe is less than the predetermined threshold value, then a low-speed, high-accuracy algorithm is chosen instead in operation 730.

Figure 8:
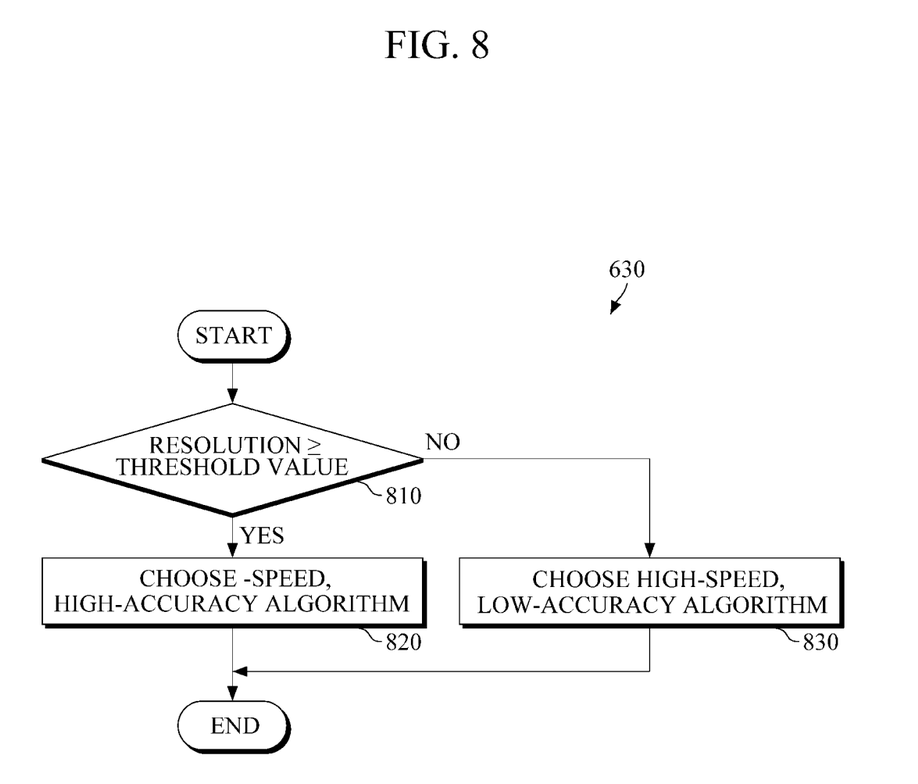
FIG. 8 is a flowchart illustrating another example of an operation of FIG. 6 in which an image analysis algorithm is selected.

FIG. 8 is a flowchart illustrating another example of the image algorithm selection process 630 in FIG. 6.

Referring to FIG. 8, the image analysis algorithm selection process 630 may otherwise begin with the operation 810 in which the resolution of the current image frame is compared to a predetermined threshold value 810. If the resolution of the current image frame is equal to or higher than the predetermined threshold value, a low-speed, high-accuracy algorithm is selected to be used in analysis of the current image frame in operation 820. If the resolution of the current image frame is lower than the predetermined threshold value, then a high-speed, low-accuracy algorithm is chosen to be used instead in operation 830.

The apparatuses, units, modules, devices, and other components illustrated in FIGS. 1 and 2 (e.g., the image analysis algorithm selector 110, image analyzer 120, image obtainer 210, speed detector 220, and image analysis algorithm storage 230) that perform the operations described herein with respect to FIGS. 6-8 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 6-8. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 6-8 that perform the operations described herein with respect to FIGS. 1-2 are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

The screen display 240 described herein may be implemented using a liquid crystal display (LCD), a light-emitting diode (LED) display, a plasma display panel (PDP), a screen, a terminal, or any other type of display known to one of ordinary skill in the art. A screen may be a physical structure that includes one or more hardware components that provide the ability to render a user interface and receive user input. The screen may include any combination of a display region, a gesture capture region, a touch-sensitive display, and a configurable area. The screen may be part of an apparatus, or may be an external peripheral device that is attachable to and detachable from the apparatus. The screen display may be a single-screen display or a multi-screen display. A single physical screen may include multiple displays that are managed as separate logical displays permitting different content to be displayed on separate displays even though they are part of the same physical screen.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A computer-aided diagnostic (CAD) apparatus comprising:
   at least one processor; and
   at least one memory storing one or more computer programs configured to be executed by the at least one processor, the one or more computer programs including instructions to:
   select an image analysis algorithm based on a speed of a probe or a resolution of a current image frame obtained by the probe, and
   detect and classify a region of interest (ROI) in the current image frame using the selected image analysis algorithm.

2. The CAD apparatus of claim 1, wherein the at least one processor is further configured to:
   select a first image analysis in response to the speed of the probe being equal to or greater than a predetermined threshold value, and
   select a second image analysis in response to the speed of the probe being less than the predetermined threshold value.

3. The CAD apparatus of claim 2, wherein the first image analysis algorithm is a high-speed, low-accuracy algorithm relative to the second image analysis algorithm, and the second image analysis algorithm is a low-speed, high-accuracy algorithm relative to the first image analysis algorithm.

4. The CAD apparatus of claim 2, wherein the first image analysis algorithm and the second image analysis algorithm are distinguished from each other based on at least one of the following factors: whether image-preprocessing is performed, a level of image-preprocessing performed, the size of a sub-image used in image analysis, the complexity of the image analysis algorithm, whether analysis results of previous image frames are applied to the image analysis, a degree to which the analysis results of the previous image frames are utilized, and types and number of extractable features of the image analysis.

5. The CAD apparatus of claim 1, wherein the at least one processor is further configured to: select the first image analysis algorithm in response to the resolution of the current image frame being lower than a predetermined threshold value, and select the second image analysis algorithm in response to the resolution of the current image frame being equal to or higher than the predetermined threshold value.

6. The CAD apparatus of claim 1,
wherein the at least one processor is further configured to detect a speed of the probe.

7. The CAD apparatus of claim 6, wherein the at least one processor is further configured to detect the speed of the probe based on at least one of following factors: a difference between a sum of image intensities per pixel in a previous image frame and a sum of image intensities per pixel in the current image frame, a difference between a histogram of the current image frame and a histogram of the previous image frame, altering information between the previous and current image frames of a salient region, a sensor value obtained by an acceleration sensor equipped in or on the probe, and the resolution of the current image frame.

8. The CAD apparatus of claim 1, further comprising:
a screen configured to display an ROI detection result and an ROI classification result.

9. The CAD apparatus of claim 8, wherein the screen is further configured to display information about the speed of the probe and the selected image analysis algorithm.

10. The CAD apparatus of claim 9, wherein the information about the image analysis algorithm includes at least one of the following items: a type of image analysis algorithm, an indication of whether image-preprocessing is performed, a level of image-preprocessing performed, a size of a sub-image used in image analysis, a structure or complexity of the image analysis algorithm, an indication of whether analysis results of previous image frames are applied to the image analysis, a degree to which the analysis results of the previous image frames are utilized, and accuracy of the image analysis.

11. An computer-aided diagnosis (CAD) method comprising:
selecting, using at least one processor, an image analysis algorithm based on a speed of a probe or a resolution of a current image frame obtained by the probe; and
detecting and classifying, using the at least one processor implementing the selected image analysis algorithm, a region of interest (ROI) in the current image frame.

12. The CAD method of claim 11, wherein the selecting of the image analysis algorithm comprises: selecting a first image analysis algorithm in response to the speed of the probe being equal to or greater than a predetermined threshold value, or selecting a second image analysis algorithm in response to the speed of the probe being than the predetermined threshold value.

13. The CAD method of claim 12, wherein the first image analysis algorithm is a high-speed, low-accuracy algorithm relative to the second image analysis algorithm, and the second image analysis algorithm is a low-speed, high-accuracy algorithm relative to the first image analysis algorithm.

14. The CAD method of claim 12, wherein the first image analysis algorithm and the second image analysis algorithm are distinguished from each other based on at least one of the following factors: whether image-preprocessing is performed, a level of image-preprocessing performed, a size of a sub-image used in image analysis, a complexity of the image analysis algorithm, whether analysis results of previous image frames are applied to the image analysis, a degree to which the analysis results of the previous image frames are utilized, and types and a number of extractable features.

15. The CAD method of claim 11, wherein the selecting of the image analysis algorithm comprises: selecting the first image analysis algorithm in response to the resolution of the current image frame being lower than a predetermined threshold value, or selecting the second image analysis algorithm in response to the resolution of the current image frame being equal to or higher than the predetermined threshold value.

16. The CAD method of claim 11, further comprising:
detecting a speed of the probe.

17. The CAD method of claim 16, wherein the detecting of the speed of the probe is based on at least one of following factors: a difference between a sum of image intensities per pixel in a previous image frame and a sum of image intensities per pixel in the current image frame, a difference between the histogram of the current image frame and a histogram of the previous image frame, altering information between the previous and current image frames of a salient region, the sensor value obtained by an acceleration sensor equipped in or on the probe, and the resolution of the current image frame.

18. The CAD method of claim 11, further comprising:
outputting an ROI detection result and an ROI classification result to a screen.

19. The CAD method of claim 18, further comprising:
outputting to the screen information about the speed of the probe and the selected image analysis algorithm.

20. The CAD method of claim 19, wherein the information about the image analysis algorithm includes at least one of the following items: a type of image analysis algorithm, an indication of whether image-preprocessing is performed, a level of image-preprocessing performed, a size of a sub-image used in image analysis, a structure or complexity of the image analysis algorithm, an indication of whether analysis results of previous image frames are applied to the image analysis, a degree to which analysis results of the previous image frames are utilized, and an accuracy of the image analysis.

21. A computer-aided diagnostic (CAD) apparatus comprising:
at least one processor; and
at least one memory storing image analysis algorithms and one or more computer programs configured to be executed by the at least one processor, the one or more computer programs including instructions to:
select an image analysis algorithm among the image analysis algorithms based on a movement speed of a probe or a resolution of a current image frame obtained by the probe.

22. The CAD apparatus of claim 21, wherein the image analysis algorithms are classified based on a provided analysis accuracy and an analysis speed.

23. The CAD apparatus of claim 21, wherein the image analysis algorithms comprise a first image analysis algorithm that is classified as a high-speed, low-accuracy algorithm, and a second image analysis algorithm that is classified as a low-speed, high-accuracy algorithm.

* * * * *